United States Patent [19]

Constancis et al.

[11] Patent Number: 5,496,872

[45] Date of Patent: Mar. 5, 1996

[54] ADHESIVE COMPOSITIONS FOR SURGICAL USE

[75] Inventors: Alain Constancis, Lyons; Gérard Soula, Meyzieu; Jean-Louis Tayot, La Tour de Salvagny; Jérôme Tiollier, Lyons, all of France

[73] Assignee: Imedex, Chaponost, France

[21] Appl. No.: 277,069

[22] Filed: Jul. 19, 1994

[30] Foreign Application Priority Data

Jul. 21, 1993 [FR] France .................... 93 08964

[51] Int. Cl.$^6$ .................... A61K 38/00; A61L 25/00; C08G 69/10; C08L 1/00
[52] U.S. Cl. .................... 523/118; 523/111; 523/113; 524/606; 528/313; 528/318; 528/328; 514/626; 514/712; 530/300; 602/50
[58] Field of Search .................... 523/111, 118; 524/606; 528/313, 318, 328; 514/626, 712; 602/50; 530/300

[56] References Cited

U.S. PATENT DOCUMENTS

| | | | |
|---|---|---|---|
| 4,017,598 | 4/1977 | Ohno et al. | 424/439 |
| 4,177,254 | 12/1979 | Khan et al. | 424/439 |
| 4,407,787 | 10/1983 | Steinberger | 424/28 |
| 5,026,821 | 6/1991 | Boussta et al. | 528/350 |
| 5,041,497 | 8/1991 | Bhattacharjee et al. | 528/325 |

*Primary Examiner*—Paul R. Michl
*Assistant Examiner*—Andrew E. C. Merriam
*Attorney, Agent, or Firm*—Larson and Taylor

[57] ABSTRACT

The invention relates to an adhesive, biocompatible, biodegradable and non-toxic composition for surgical use, in particular for binding tissues, which composition is of the following general formula:

$$R_3-S-(CH_2)_x-\underset{\underset{R_1}{\overset{\mid}{C=O}}}{CH}-NH-\overset{\overset{\mid\mid}{O}}{C}-R-\overset{\overset{\mid\mid}{O}}{C}-NH-\underset{\underset{R_2}{\overset{\mid}{C=O}}}{CH}-(CH_2)_y-S-R_4 \quad (I)$$

in which:

R is a hydrocarbon chain containing from 1 to 50 carbon atoms, $R_1$ and $R_2$ are identical or different and are chosen from the following groups:

$$-O-R_5;\ -NH-\underset{COOR_7}{\overset{\mid}{CH}}-(CH_2)_z-S-R_6;\ -NH-(CH_2)_y-S-R_6$$

$R_3$, $R_4$, $R_5$, $R_6$ and $R_7$ independently represent hydrogen or an aliphatic and/or alicyclic and/or aromatic group, $$CH_3;\ -CH_2-CH_3;\ -CH_2-\phi;\ -C\underset{\phi}{\overset{\phi}{\diagdown}}^{\phi}$$

17 Claims, No Drawings

ADHESIVE COMPOSITIONS FOR SURGICAL USE

The present invention relates to new adhesive compositions comprising compounds resulting, for example, from the condensation of a carboxylic diacid with a sulphur-containing amino acid or one of its derivatives. These products contain reactive thiol SH functions which may oxidize to form disulphide bridges, leading to polymers which may or may not be crosslinked.

Biodegradable synthetic oligomers and polymers are already known, which very often consist of simple hydrolysable (ester or amide) chains of compounds capable of being degraded, forming metabolites.

Thus, Patent Application EP 0,332,530 describes hydrophilic polymers with a degree of polymerization of less than 1000, preferably between 20 and 300, and which consist of the polyamides resulting from the condensation of citric acid with diamines, such as lysine, cystamine and cystine.

The synthesis of these polyamides presents real difficulties associated with the protection and then the deprotection of citric acid.

These biodegradable polyamides may be used for the preparation of medicament carriers, sutures, ligatures or prostheses, or alternatively of surgical adhesives.

If, for certain applications, the use of polymers of relatively high mass, of the type of those described in Patent Application EP 0,332 530, is advantageous for other uses, the use of monomers or oligomers bearing reactive or polymerizable functions (prepolymers) is preferable. This is particularly the case in reparatory surgery (bone-filling, surgical cements, biological adhesives etc.) or in dental surgery (dental cements etc.). In these applications, it is advantageous for the monomer or prepolymer to be able to defuse very readily into the tissue to be repaired and thus to penetrate into all the interstitial spaces. The polymerization may then occur "in situ" and give rise to an interlocking of the polymer chains which have the desired filling, cohesion or adhesion properties.

In this state of the art, one of the essential aims of the invention is to provide synthetic organic products which are biocompatible and biodegradable surgical adhesives based on non-toxic products.

Another essential aim of the invention is to provide such products comprising synthetic organic products which are found in the form of prepolymers and/or monomers, capable of diffusing readily into biological tissues and of polymerizing in situ, or even in vivo, in order satisfactorily to ensure the adhesion functions.

These aims and others are achieved by the present invention which relates, in the first place, to a biocompatible, biodegradable and non-toxic adhesive composition for internal or external surgical use, which comprises an organic product containing at least two thiol functions or derivatives and carboxylic functions, which may be protected or unprotected, and/or carbonyl functions, of the following general formula:

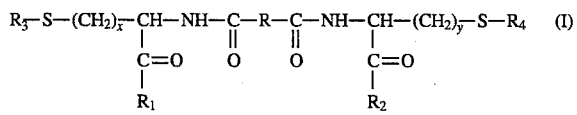

in which:

R is a hydrocarbon, preferably alkylated, chain containing from 1 to 50 carbon atoms and even more preferably an aliphatic chain having from 1 to 10 carbon atoms, $R_1$ and $R_2$ are identical or different and are chosen from the following groups:

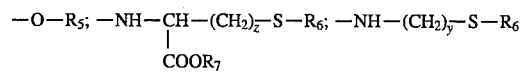

$R_3$, $R_4$, $R_5$, $R_6$ and $R_7$ independently represent hydrogen or an aliphatic and/or alicyclic and/or aromatic group, preferably a lower alkyl group and/or an aromatic group and, even more preferably, one of the following groups:

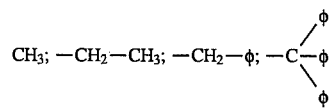

x, y and z=1 or 2.

For reasons of simplicity, the aromatic rings are denoted by the Greek letter φ throughout the present account.

In the sense of the present invention, the term "lower alkyl" denotes radicals containing from 1 to 6 carbon atoms.

The biological compounds corresponding to this formula advantageously have a relatively low molecular weight (less than 2000) and may thus diffuse readily through the protein networks (collagen, elastin etc.) or glycoprotein networks constituting the tissues. This is a property which it is advantageous to exploit in the field of adhesives.

A first sub-class of the products used in the context of the invention comprises those in which the radicals $R_1$ and $R_2$ represent $OR_5$.

Even more precisely, when $R_3$ and $R_4$ correspond to hydrogen, this gives an oligomer which has, at each of its two ends, an SH function borne by a cysteine unit or derivative ("di SH" oligomer).

These SH functions have the capacity to react with themselves, in order to form disulphide bridges and to allow long chains to be obtained. This property may be exploited in order to prepare various adhesive products such as threads, films or viscous solutions which are biodegradable.

The presence of carboxylic functions on these di SH compounds makes it possible to envisage interactions with other molecules (for example natural macromolecules). This tends towards an improvement in the adhesive properties. In addition, these carboxylic functions lead to a hydrophilic nature and a capacity to bind active principles.

A second sub-class which is typical of the products used in the context of the invention regroups the products corresponding to the general formula indicated above, in which the radical $R_1$ represents:

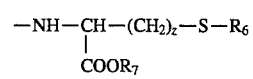

and $R_2$ represents $—O—R_5$ or vice versa.

When $R_5$ and $R_6$ consist of hydrogen, these oligomer compounds may be termed as "tri SH" oligomers. These oligomers, the SH ends of which are capable of reacting to form disulphide bridges, allow possibilities of development of multidirectional networks to be glimpsed, which can improve the mechanical properties, the virtues of adhesion and the resistance to biodegradation of the products according to the invention.

A third sub-class of organic products which are used in the context of the invention consists of the products in which the radicals $R_1$ and $R_2$ consist of the radical:

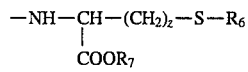

When $R_3$, $R_4$ and $R_6$ correspond to hydrogen, a tetrafunctional oligomer is defined which contains four SH units at its ends ("tetra SH" oligomer). This multiplicity of potential attachment points may be exploited advantageously in the field of biomaterials. This is an extension of that which has been indicated above for the di- and trifunctional oligomers.

The cysteic unit used may be formed by cysteine itself: x, y and z=1 or by homocysteine: x, y and z=2, which may optionally originate from cystine or homocystine.

The alkylated chain R, which is optionally substituted, defines the radical:

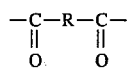

in the formula (I), such that it belongs to the class of polycarboxylic, advantageously dicarboxylic, acid residues, with the exclusion of citric acid, R preferably being selected from the following groups:

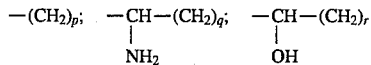

with:

$p \leq 5$, preferably equal to 2 (succinic acid) or 3 (glutaric acid), $q \leq 5$, preferably equal to 1 (aspartic acid) or 2 (glutamic acid), and finally $r=5$, preferably equal to 1 (malic acid).

R may also be composed of low-molecular-weight polylactic and/or polyglycolic and/or polyamino acid chains.

These oligomers which are used in the context of the invention bear SH functions which impart to them capacities for polymerization and/or crosslinking, optionally in the presence of an oxidizing agent. They thus make it possible to obtain, after oxidation, polymers which may or may not be crosslinked, which may be used as biomaterials and may possibly be degraded to natural metabolites, i.e. which are involved in the biological cycles of mammals.

Moreover, their size and their structure are such that they may readily migrate and penetrate into mammalian biological tissues.

It follows that these oligomers may gain access without difficulty to the target biological sites and may polymerize "in situ" so as to form interlocking system and/or a network of polymer chains.

These oligomers thus find their use as constituents of the adhesive materials or compositions according to the invention.

In addition, the polymerization of these products by oxidation of the SH's to disulphide bridges may also be carried out in vitro and may thus allow the formation of mouldable articles or films, which may be used as biomaterials remaining adhesive.

The present invention also relates to an adhesive biomaterial comprising one or more polymers which are capable of being obtained from oligomers, as described above and which correspond to the following general formula:

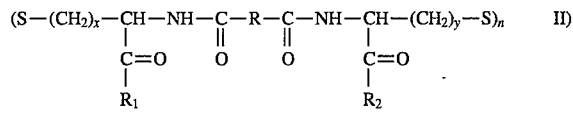

in which:

$R_1$ and $R_2$ are identical or different and are chosen from the following groups:

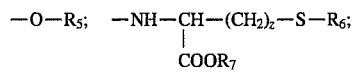

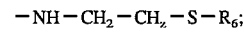

with $R_5$, $R_6$ and $R_7$ independently representing hydrogen or an aliphatic and/or alicyclic and/or aromatic group, preferably a lower alkyl group and/or an aromatic group and, even more preferably, one of the following groups:

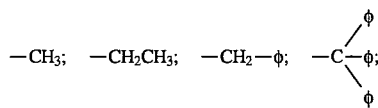

R is chosen such that the radical:

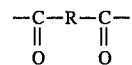

of the formula (I) is a radical belonging to the class of polycarboxylic, advantageously dicarboxylic, acids with the exclusion of citric acid, preferably selected from the following groups:

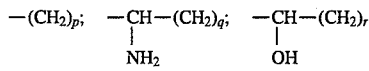

with:

$p \leq 5$, preferably equal to 2 or 3, $q \leq 5$, preferably equal to 1 or 2, and $r \leq 5$, preferably equal to 1, n being between 1 and 100, preferably between 2 and 50 and, even more preferably between 4 and 30, and x and y corresponding to 1 or 2 as above.

R may also be composed of low-molecular-weight polylactic and/or polyglycolic and/or polyamino acid chains.

These polymers are polysulphides in which the recurring unit preferably results from the combination of succinic acid and cysteine.

These polymers may serve as a base for obtaining other adhesive products in accordance with the invention by constituting crosslinked materials (III). This cross-linking is carried out, for example, by amidation and/or esterification, using at least one bridging agent, preferably chosen from the following products: cystine, lysine, cystamine and their derivatives, monosaccharides and their hydrogenated derivatives, and other polyols (glycerol).

The invention also relates to, as new products, the adhesive biomaterials containing the crosslinked materials (III) which have been crosslinked by bridges originating from at least one bridging agent of the type of that mentioned above.

Given that all the products in accordance with the invention described above may be incorporated into the same preparation chain, it is clear that the present invention also relates to any bioadhesive composition consisting of a mixture of at least two of the abovementioned products, including the mixture of a polymer or of a crosslinked material with a non-solid product as described above, or by impregnation of such a polymer or crosslinked material using such a non-solid product.

The glues according to the invention are biocompatible and have proved to be particularly suitable for entry into the biomaterials composition.

Another subject of the present invention is thus any adhesive biomaterial formed from a mixture and/or a combination of at least one of the oligomers (I) and/or polymers (II) and/or crosslinked materials (III) and/or compositions described above with biological macromolecules, biodegradable, synthetic or natural polypeptides such as:

polysaccharides; e.g. starch, cellulose, chitosan, dextran, mucopolysaccharides such as hyaluronic acid or chondroitin sulphate;

proteins; e.g. collagen, gelatin, albumin, globulins;

polyamino acids; polyesters (in particular lactic and/or glycolic polyesters), polyortho esters, polyanhydrides, polyphosphazines;

and lipids and phospholipids.

In these mixtures and/or combinations, these macromolecules may be engaged in physical and/or chemical bonds with the products I, II, III and the compositions according to the invention.

These adhesive biomaterials may be glues or gluing materials in any physical form, including the solid form.

The compositions according to the invention may be used, in vitro or in vivo, for binding biological tissues to each other or for binding between a biological tissue and an implanted biomaterial, including when the biological tissue is highly hydrated.

In a first embodiment, the composition is provided in liquid solution form, for example in bottle or spray form, or in a form analogous to the liquid form, for example in gel form or in the form of very small-sized particles. In this embodiment, the adhesion functionality is ensured by a polyfunctional monomer (multi-SH and multi-COOH) which can diffuse into the biological tissues to be stuck.

In order to ensure setting of the glue thus produced, an oxidizing agent capable of inducing the polymerization of this monomer is brought in. This oxidizing agent may be, for example, a solution of iodine, of hydrogen peroxide, an oxidizing enzyme (oxidase) or even oxygen itself, in pure form or in atmospheric form.

The composition may be provided, for example, in kit form comprising, in one container, the adhesive composition and, in the other, an oxidizing agent.

For the binding together of tissues or for the binding of a tissue and an implanted biomaterial, consisting in applying the two surfaces to be joined one against the other, a composition and/or an oxidizing agent is applied or allowed to diffuse over at least one of the said surfaces, under conditions such that the oxidizing agent brings about a polymerization of the composition at the moment the said surfaces are applied one against the other. For example, the composition may be applied to one surface and the oxidizing agent to the other. Or alternatively, the oxidizing agent is applied first only on one or the two surfaces and then the composition is subsequently applied between the two tissues.

It is also possible to mix the composition and the oxidizing agent at the time of introduction, or slightly before this moment, for example by using a double syringe or any other device for extemporaneous mixing.

Irrespective of the load and the sequence of the applications to the surfaces, the result should be such that the oxidizing agent and the composition are in intimate contact at the two surfaces to be joined, the composition and/or the agent preferably being designed in a form which allows a certain diffusion from the surface towards the interior of the tissue.

In another embodiment, the composition is provided in the form of a bulk material, the geometrical form of which may be very variable. It may be, for example, a film or a textile, a sponge, a patch or any other form. In this embodiment, in which the composition is in bulk solid form, the organic product is advantageously a polymer according to the formula (II) which has adhesive properties.

The compositions according to the invention may be combined with a biomaterial, which is preferably resorbable, in order to form a biomaterial complex presenting, superficially or within its depth, an adhesive composition according to the invention. The composition may be provided in or on the biomaterial, either by being incorporated during the manufacture of the biomaterial or by impregnation, coating or any other process.

The biomaterial, with which the composition is combined, may form only one bioresorbable carrier, for example one made of collagen, which may have any physical form, for example a suspension, ballotini, gel, film, sponge or patch form, in order to form, with the composition, the biomaterial complex intended to be applied between the tissues. However, as a variant, this biomaterial may form a prosthesis or another, more hard-wearing component, for example a filling agent, combined with the composition according to the invention, allowing it to be stuck to one or more tissues. These biomaterial complexes are introduced into the tissue, or between the tissues, in the presence of an oxidizing agent.

The invention also relates to the abovementioned biomaterials, lacking any composition according to the invention, these biomaterials presenting, superficially or within their depth, an oxidizing agent which is intended to react with a composition according to the invention. In this case, the gluing is carried out by bringing a composition which is, for example, liquid or in gel form, in contact with the biomaterial or with the tissue surface against which the biomaterial is applied, so as to bring about the reaction between the oxidizing agent and the composition.

The non-adhesive biomaterial with which the adhesive composition according to the invention is combined in order to form a complete adhesive biomaterial may consist of or contain any biocompatible material, and preferably made of collagen. However, in an advantageous variant, this biomaterial may itself consist mainly or entirely of a polymer, which is adhesive or non-adhesive, according to the formula (II) or of a crosslinked material (III) with which an adhesive composition or material according to the invention is combined by mixing or by any other means.

Indeed, the polymer according to the formula (II) may be produced under conditions leading to a polymerization which leaves behind few or no adhesive functions.

The production of the adhesive products (I), (II) and (III) is incorporated into a reaction scheme developed by the French company FLAMEL TECHNOLOGIES SA and which is as follows: the first step is the preparation of polymers including, in particular, those corresponding to the formula (II), which subsequently give access to the products (I), which themselves may be reconverted to polymers (II) or to crosslinked materials (III).

This preparation preferably consists in carrying out:
a) a polycondensation between:
on the one hand, a reactant of formula A:

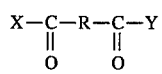

with X and Y, which may be identical or different and represent a halogen, preferably chlorine, or a radical —$OR_8$, in which $R_8$ corresponds to hydrogen or to an alicyclic or aliphatic radical, preferably chosen from the following list of radicals:

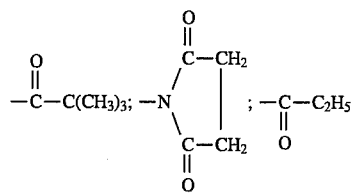

and with a radical R which is a hydrocarbon, preferably alkylated, chain containing from 1 to 50 carbon atoms and, even more preferably, an aliphatic chain having from 1 to 10 carbon atoms, and, on the other hand, a reactant of formula B:

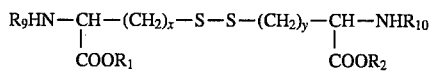

with $R_1$ and $R_2$ corresponding to an identical definition to that given above, with $R_9$ and $R_{10}$ identical or different and chosen from the following radicals: H, aliphatics, preferably alkyles, hydrogen being still the most preferably retained, and with x and y being, in a conventional manner, equal to 1 or 2, b) a reduction of the polymer obtained, which may or may not be subsequently converted.

In practice, it is preferable for the compound of formula A to be in the form of an acid halide, for example an acid chloride, and for the compound B of cysteic nature to be esterified with alkyl radicals $R_1$ and $R_2$ which preferably consist of methyl radicals.

Two polycondensation techniques may be envisaged in order to obtain polymers including those of formula (II): solution polycondensation or interfacial polycondensation.

These techniques will be viewed in detail in the examples below.

Once the polymer has been obtained, it is advantageous to hydrolyse the ester functions carried by this polymer. This hydrolysis is performed in water, in a mildly alkaline medium, in order to maintain control over the functions other than the ester functions of the polymer (saponification).

According to a first variant of the process, the polymer, which may or may not have undergone a hydrolysis of its ester functions, is subjected to a reduction of the disulphide bridges which it contains, thus mainly allowing difunctional oligomers bearing an SH unit at each of their ends to be obtained.

Standard reduction techniques are used. They may be, for example, those described in METHODS IN ENZYMOLOGY, vol. 143, "Sulfur and sulfur amino-acids", W. B. JAKOBY, O. W. GRIFFITH, Academic Press Inc., Orlando, (1987).

According to a second variant of the process, the polymer which has been partially or totally saponified is subjected to a crosslinking. This polymer may be the polycondensate as it is or reduced in accordance with the first variant of the process, which corresponds to the di-SH difunctional oligomers. The crosslinking is performed using at least one bridging agent and preferably in the presence of a coupling agent.

The bridging agent is preferably a diol or a diamine which has at least one —S—S—bond, such as for example the cystine dialkyl ester (methyl or ethyl ester).

The coupling agent is advantageously chosen from the following list of compounds: ethyldiaminopropyl-carbodiimide (EDC), carbonyldiimidazole (CDI).

The degree of crosslinking may be made to vary by acting upon the amount of bridging agent used relative to the number of acid functions of the polymer.

The concentration of bridging agent is defined by the following ratio: number of $NH_2$, OH, etc. functions of the bridging agent number of COOH functions of the polymer This ratio is between 0.01 and 1.

The crosslinked materials (III) obtained may be represented symbolically as follows:

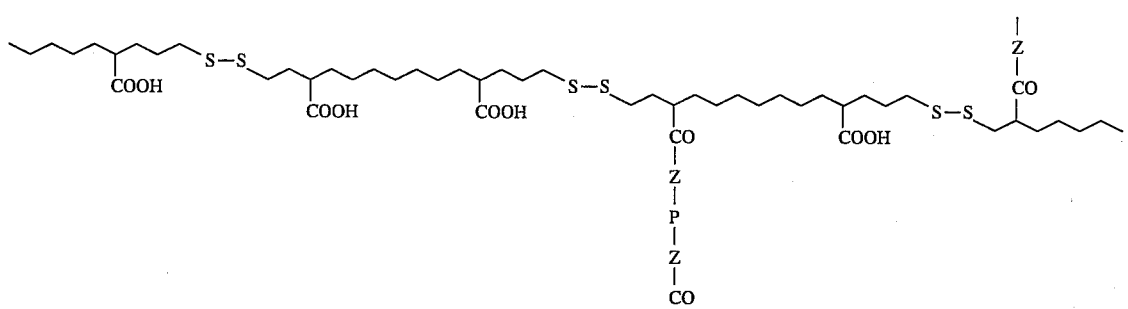

-continued

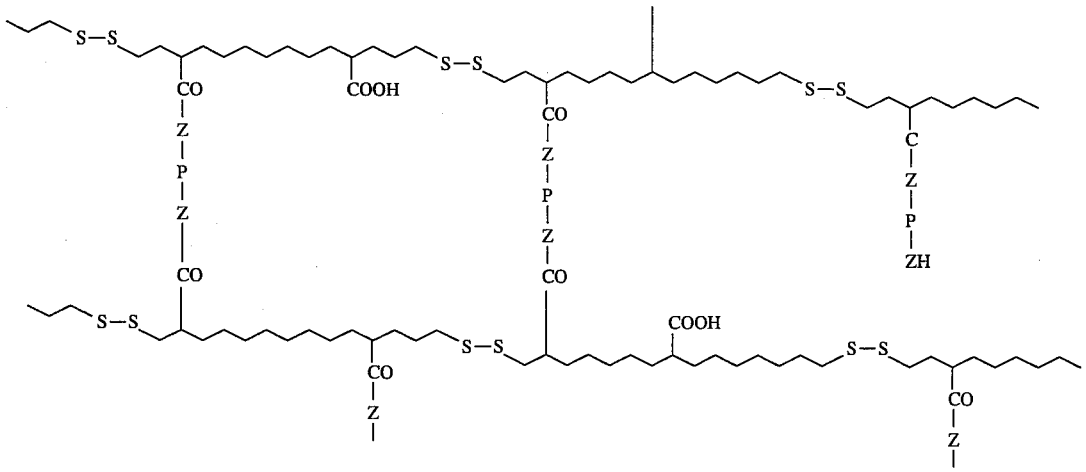

with Z=O or NH.

—Z—P—Z— is a bridge derived from polyols (Z=O): OH—P—OH or from polyamides (Z=NH): $H_2N$—P—$NH_2$.

The reduction of such a crosslinked material may be performed in suspension in water, in the presence of dithiothreitol or tributylphosphine. It leads to a mixture of molecules containing several —SH functions which may be isolated, freeze-dried and stored under nitrogen at a temperature below 0° C. It is subsequently possible, under mild oxidation conditions, to reform the disulphide bridges in order to obtain a crosslinked material similar to (III).

In the particular case in which the bridging agent is chosen from the following products: cystamine or esters of cystine or of homocystine, the P groups of the crosslinked material (III) also contain disulphide bridges and the reduction of the crosslinked material then leads to a mixture mainly composed of the di-, tri- and tetra-SH molecules described above (formula I).

The last phase of the process, which is common to the two abovementioned variants, consists in oxidizing the SH oligomers obtained in the above step, so as to produce polymers, including in particular those of formula (II), and/or crosslinked materials (III), by (re) forming the disulphide bridges.

This oxidation is carried out either, and preferably, in the presence of at least one oxidizing system comprising, for example, iodine and/or its derivatives and/or hydrogen peroxide or an enzymatic system, or by electrochemistry, or directly in air.

The object of the present invention is also any adhesive composition formed by a mixture of at least two products of formula (I) and/or (II) and/or (III).

In particular, the advantageous compositions are those comprising mixtures of oligomers (I), because once reoxidized they lead to the biomaterials, gels and multi-SH coatings described above. These reoxidized compounds should exhibit a certain number of mechanical properties, in relation with their usual characteristics. The level of the mechanical properties essentially depends on the structure of the network formed and on the control over the crosslinking of the multi-functions, preferably the multi-SH functions, of the oligomers. In theory, any multi-SH composition with a mean SH functionality which is strictly greater than 2 may give an insoluble crosslinked material. The mean SH functionality may be defined as follows:

$F_{mean}$= number of SH units per molecule=A/B with:
A=1. number of mono-SH molecules+2. number of di-SH molecules+3. number of tri-SH molecules+4. number of tetra-SH molecules,
B=number of mono-SH molecules+number of di-SH molecules+number of tri-SH molecules+number of tetra-SH molecules.

Taking into account the possibility of intramolecular reactions which disrupt the formation of the network by consuming potential nodes, it is preferable to aim for $F_{mean}$'s for the oligomer mixtures of the order of 2.1 to 2.5, in order to ensure the formation of the network. Generally speaking, the elasticity and the swelling (gel aspect) of the crosslinked material decreases when $F_{mean}$ increases.

A desired mean functionality (for example 2.3) may be obtained directly or indirectly.

According to the direct method, linear polycondensates of known length are crosslinked in order to estimate the relative proportion of mono-SH relative to the di-SH's, with an adapted amount of bridging agent, such as cystine dimethyl ester. After reduction of the crosslinked material obtained, this provides a mono-, di-, tri- and tetra-SH mixture for which the $F_{mean}$ will be close to that desired. It is necessary to ensure, however, that the bridging agent has totally reacted and that the SS bridges have been totally reduced.

The indirect method consists in "over-crosslinking" a linear polymer by aiming for a theoretical $F_{mean}$, for example in the region of 3, in reducing this cross-linked material, in determining the $F_{mean}$ obtained by assay, in preparing, by reduction of a linear polycondensate, a mono- and di-SH mixture which is close to 2 and in obtaining, by mixing the two assayed compositions in the desired proportions, the $F_{mean}$ corresponding to an optimum for the properties sought.

For the applications of biomaterials requiring the formation of a gel, it would appear to be desirable to start from a composition, i.e. an oligomer mixture having an $F_{mean}$ greater than or equal to 2, preferably less than or equal to 2.6 and, even more preferably, less than or equal to 2.3.

For harder adhesive biomaterials, it would appear to be desirable to aim for $F_{mean}$'s greater than or equal to 2.3 and preferably greater than or equal to 2.5.

The oligomers (I), polymers (II) inter alia, and crosslinked materials (III), which may or may not be functionalized, are compounds which exhibit no direct or indirect toxicity: they are not carcinogenic, teratogenic, immunogenic or mutagenic. Moreover, they are perfectly biodegradable, that is to say that they consist of products which are integrated perfectly well into metabolic pathways (in particular the Krebs cycle) of man or animals. The degradation products of these compounds are, ipso facto, perfectly tolerated.

In particular, it is interesting to note that the oligomers (I) are of low molecular weight (lower than 1000 Da) and they are thus capable of diffusing into the interior of biological tissues to be subsequently polymerized and/or crosslinked therein. The interlocking which may then form with the glycoproteins ensures a solid adhesive bond.

In reduced form and combined with an oxidizing system, these products and/or their mixtures are very suitable as adhesive biomaterials or as biological glues. These constituents enter into the field of the invention.

In oxidized form, these constituents are cohesive networks, dotted with disulphide bridges and having between them variable mechanical and biological properties.

Another subject of the invention is the use of the products of formula (I) or (II), or of the cross-linked materials (III) for the preparation of an adhesive, biocompatible, biodegradable and non-toxic composition, for surgical use.

Examples 1 to 20 which follow are an illustration of the properties and of the variants of the adhesives according to the invention. They also describe the structures and the methods for preparing the products entering into the adhesive composition according to the invention.

EXAMPLES

EXAMPLE 1

SYNTHESIS OF THE POLYMER (1) BY SOLUTION POLYCONDENSATION IN DIMETHYLACETAMIDE (DMAC) OF CYSTINE DIMETHYL ESTER HYDROCHLORIDE AND SUCCINYL CHLORIDE.

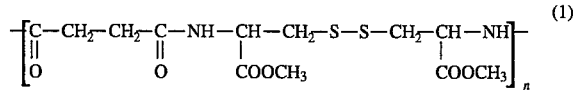
(1)

25 g (0.073 mol) of cystine dimethyl ester hydrochloride and 400 ml of DMAC are placed in a 1 l reactor. 41.2 ml of triethylamine (0.293 mol) are then added. 8.1 ml of freshly distilled succinyl chloride are diluted in 100 ml of DMAC and this is all added to the reaction mixture using a dropping funnel. The reaction mixture is then stirred for 24 hours at room temperature. The precipitated triethylammonium salt is removed by filtration and the reaction mixture is then precipitated in 5 l of water. The polymer is recovered by filtration and oven-dried under vacuum: 13 g of a white (slightly pink-coloured) powder are thus obtained. The $^1$H NMR (in deuterated trifluoroacetic acid (TFA)) and IR spectra are in accordance. The molecular weights, determined by steric exclusion chromatography (SEC) in DMAC and expressed as polystyrene equivalents, are as follows:

$M_a$=6200, $M_w$=9600

EXAMPLE 2

SYNTHESIS OF THE POLYMER (1) BY WATER/TOLUENE INTERFACIAL POLYCONDENSATION OF CYSTINE DIMETHYL ESTER HYDROCHLORIDE AND SUCCINYL CHLORIDE.

25 g (0.073 mol) of cystine dimethyl ester hydrochloride and 200 ml of DMAC are placed in a 1 l reactor. 31.06 g of anhydrous sodium carbonate (0.293 mol) are then added. A pre-emulsion is subsequently formed by addition of 100 ml of toluene. 8.1 ml of freshly distilled succinyl chloride are then diluted in 100 ml of toluene and this is all added to the reaction mixture using a dropping funnel. The reaction mixture is then stirred for 4 hours at room temperature. The polymer, which has precipitated during the reaction, is recovered by filtration and washed with acetone, then with water. It is oven-dried under vacuum: 14 g of a white (slightly pink-coloured) powder are thus obtained. The $^1$HNMR (in TFA) and IR spectra are in accordance and are analogous to those obtained for the polymer of Example 1. The molecular weights, determined by SEC in DMAC and expressed as polystyrene equivalents, are as follows:

$M_a$=5700, $M_w$=11,500

EXAMPLE 3

HYDROLYSIS OF THE ESTER FUNCTIONS OF THE POLYMER (1): PRODUCTION OF POLYMER (2)

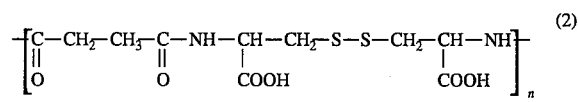
(2)

5 g of polymer (1) obtained by solution or interfacial polycondensation are suspended in 1 l of water. The pH is adjusted to 10.5 with 1M sodium hydroxide and is maintained at this value throughout the hydrolysis. The addition of sodium hydroxide is stopped when the solution becomes clear. The solution is then acidified to a pH<3 by an acidic ion-exchange resin. It is concentrated, frozen and then freeze-dried. 4.6 g of a white powder are obtained. The $^1$H NMR (in TFA and in $D_2O$) and IR spectra are in accordance and show that the hydrolysis of the ester functions is total.

EXAMPLE 4

REDUCTION OF THE POLYMER (2) BY DITHIOTHREITOL: PRODUCTION OF THE MOLECULE (3)

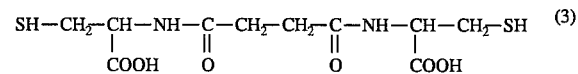
(3)

3 g of polymer (2) and 2.87 g of dithiothreitol (DTT) are dissolved in 70 ml of water under a nitrogen atmosphere. The pH is adjusted to 8.5 by addition of 1M sodium hydroxide and the solution is stirred for 3 hours under bubbling with nitrogen. The mixture is then extracted twice with 100 ml of ethyl acetate. The aqueous phase is subsequently acidified by an acidic ion-exchange resin to pH=4.5, then concentrated and precipitated in an excess of acetone. The sticky precipitate obtained is redissolved in a minimum amount of water and reprecipirated in acetone. It is finally redissolved in water and freeze-dried. 2 g of a slightly yellow product are recovered. The $^1$H NMR spectrum (in $D_2O$) obtained is in accordance with the formula (3), the carboxylic groups being in ionized form.

EXAMPLE 5

REDUCTION OF THE POLYMER (2) BY TRI(n-BUTYL)-PHOSPHINE: PRODUCTION OF THE MOLECULE (3)

2.4 g of polymer (2) are dissolved in 30 ml of water under a nitrogen atmosphere. 120 ml of methanol, degassed beforehand, are then added. Next, 2 ml of tri(n-butyl)phosphine are injected into the reaction mixture. After reacting for 3 hours, the methanol is evaporated off using a rotary evaporator. 50 ml of water are added to the residual aqueous solution, which is subsequently extracted twice with 200 ml of ethyl acetate. The aqueous solution is subsequently acidified and precipitated in acetone, as described in Example 4. The $^1$H NMR spectrum in $D_2O$ is identical to that of the product obtained in Example 4.

EXAMPLE 6

CROSSLINKING OF THE POLYMER (2) BY CYSTINE DIMETHYL ESTER 5 g of polymer (2) and 5.3 g of cystine dimethyl ester hydrochloride are dissolved in 100 ml of water. 6 g of N-dimethylaminopropyl-N'-ethylcarbodiimide (EDC) are then dissolved in 5 ml of water and immediately added to the reaction mixture. The mixture immediately turns dark red and, after a few seconds, a pink precipitate is then formed. The reaction is stopped after 3 hours and 200 ml of water are added. The precipitate is recovered by filtration, washed several times with water and then oven-dried under vacuum.

EXAMPLE 7

CROSSLINKING OF THE POLYMER (2) BY CYSTINE DIETHYL ESTER 5 g of polymer (2) and 5.73 g of cystine diethyl ester hydrochloride are dissolved in 100 ml of water. 6 g of N-dimethylaminopropyl-N'-ethylcarbodiimide (EDC) are then dissolved in 5 ml of water and immediately added to the reaction mixture. The reaction is stopped after 3 hours and 200 ml of water are added. The precipitate is recovered by filtration, washed several times with water and then oven-dried under vacuum.

EXAMPLE 8

REDUCTION BY DITHIOTHREITOL OF THE CROSSLINKED POLYMER OF EXAMPLE 6

1 g of the crosslinked polymer of Example 7 and 1.1 g of dithiothreitol are dissolved in 50 ml of water, which has been flushed beforehand with a stream of nitrogen. The pH is adjusted to 9.5 by 1M sodium hydroxide. The reaction mixture becomes clear and the reaction is stopped at the end of one hour. After six extractions with 50 ml of ethyl acetate, the aqueous solution is acidified to pH=5 by an exchange resin, reextracted with twice 50 ml of ethyl acetate and then freeze-dried. The product obtained is a mixture mainly comprising the following molecules (3), (4) and (5):

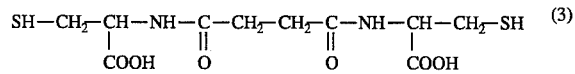

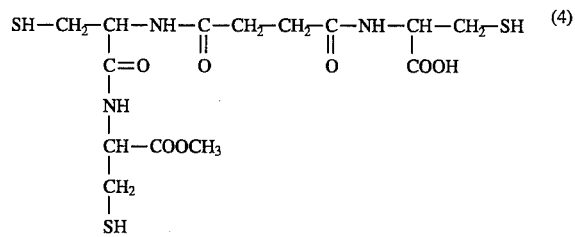

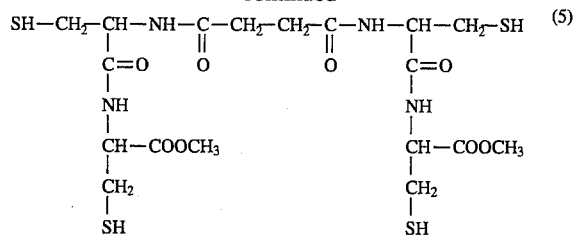

The carboxylic functions are in ionized form (—COO$^-$, Na$^+$). The mixture is no longer fully soluble in water when the pH is <3.

EXAMPLE 9

REDUCTION BY DITHIOTHREITOL OF THE CROSSLINKED POLYMER OF EXAMPLE 6—HYDROLYSIS OF THE ESTER FUNCTIONS OF THE PRODUCT OBTAINED

The reaction is performed as described in Example 8, but the reduced solution is maintained at pH=9.5 for 24 hours at 35° C. After six extractions with 50 ml of ethyl acetate, the aqueous solution is acidified to pH=5 by an exchange resin, re-extracted with twice 50 ml of ethyl acetate and then freeze-dried. The product obtained is a mixture mainly comprising the following molecules (3), (6) and (7):

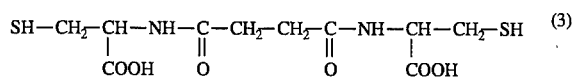

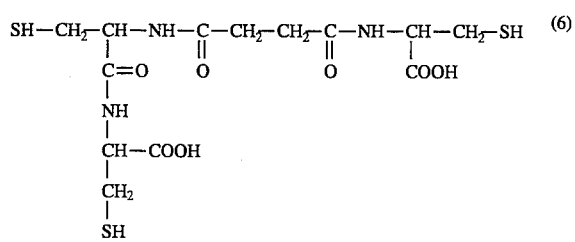

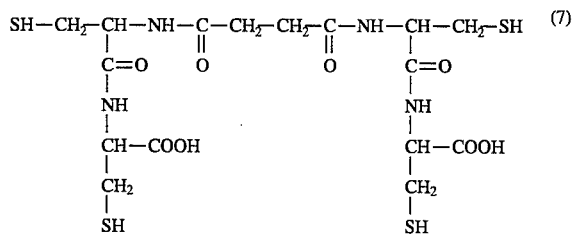

The carboxylic functions are in ionized form (—COO$^{31}$, Na$^{30}$). The mixture may be acidified (to pH=2.5) by passing through an ion-exchange resin. In this case, the water-solubility is conserved.

EXAMPLE 10

REDUCTION BY DITHIOTHREITOL OF THE CROSS-LINKED POLYMER OF EXAMPLE 7

1 g of the crosslinked polymer of Example 7 and 1.1 g of dithiothreitol are dissolved in 50 ml of water, which has been flushed beforehand with a stream of nitrogen. The pH is adjusted to 9.5 by 1M sodium hydroxide. The reaction mixture becomes clear and the reaction is stopped at the end of one hour. After six extractions with 50 ml of ethyl acetate, the aqueous solution is acidified to pH=4 with 1N HCl solution. A sticky, slightly brown precipitate is obtained. This is a mixture consisting mainly of the following molecules (3), (8) and (9):

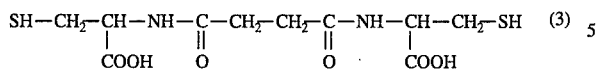

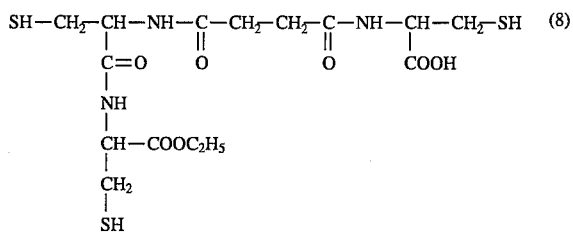

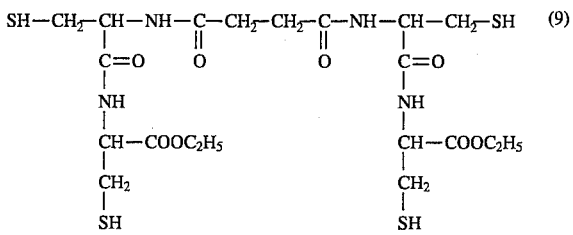

EXAMPLE 11

EX VIVO EVALUATION OF THE TISSUE ADHESION

Evaluation of the adhesive properties of the composition according to the invention was performed on rabbit muscle tissues (small of the back). These tissues are stored at 4° C. in physiological serum for a maximum of 48 hours. The rabbit tissue is cut up along the sense of the fibres using an electric slicer (thickness of the slices: 2.5 ±0.5 mm), then squares of 25 mm×25 mm are cut into the slices obtained.

The tests are performed on a usual traction apparatus, for example of Adamel Lhomargy type of DY34 type fitted with a 100N force sensor. This apparatus allows the force-displacement curves to be obtained. It also allows the maximum peel strength ($F_{max}$) and Young's modulus to be obtained, and the energy involved may be calculated from the area under the curve.

In each type of test, two test samples of rabbit tissue are attached using a cyanoacrylic glue (for example sold under the brand name Loctite superglue, liquid or gel) to inert, glass or cardboard supports which are very rigid and of larger size. The tests are performed at the end of 3 minutes after a pressure of 4N.

The composition used is a solution of the polymer, in an amount of 100 µl per sample, (2) according to Example 3, at a concentration of 20 to 25 per cent and, as a variant, not as a solution but directly as a powder onto the rabbit tissue. After gluing for 3 minutes under pressure, an adhesion value ($F_{max}$) between 1.5 and 2N is obtained. This value is advantageous and may be compared with the equivalent values of 1.5N to 2.5N of the conventional biological glues based on fibrin. The same test carried out with commercial carboxylic polymers such as polyacrylic acid and sodium alginate shows a low level of adhesion ($F_{max}<1N$, adhesional work <1 J).

EXAMPLE 12

MULTI-SH COMPOUNDS

The tests are carried out on multi-SH compounds in —COOH form, namely the compounds (3), (4), (5), (6), (7), (8) and (9) of Examples 4, 5, 8, 9 and 10, preferably (3), (6) and (7).

For this, the test sample tissues are impregnated beforehand with aqueous-alcoholic iodine solution and the composition dissolved in water, in an amount of 100 µl per sample, is then added. Depending on the test samples and the tests, the peel strength measured are between 1.12 and 3.46N, the average being 2.04 ±0.62N.

These results are thus comparable and even better on average than those of the conventional glues based on fibrin. In addition, the area under the curve, that is to say the energy used, is larger than or equal to that of the best fibrin glues.

The tests performed after one hour of contact show that the adhesional force increases with time (between 3 and 4N at the end of one hour).

EXAMPLE 13

0.1 gram of type IV human collagen (IMEDEX), dissolved in 4 ml of water, is reduced at pH 9 by 10 mg of dithiothreitol (DTT) under inert atmosphere for 18 hours. After dialysis of the solution (3 times 8 hours), 80 mg of the "multi-SH" type derivatives prepared in Example 9 are added. The pH of the solution is adjusted to 9 by addition of concentrated sodium hydroxide, and 20 microlitres of hydrogen peroxide at a concentration of 35% by weight are added to the solution in order to allow partial oxidation of the mixture. After 30 minutes, the reaction mixture is tested for adhesion by application to rabbit tissues according to the procedure described in Example 12.

After contact for 3 minutes under 4N, the following are recorded:

a mean adhesive force of 1.9 ±0.4N and an adhesional energy of 2.9 ±1.2 mJ.

The examples which follow relate to processes for binding tissues together or for binding one tissue to an implanted biomaterial by superposition of two surfaces and in which a composition according to the invention and/or an oxidizing agent is applied or allowed to diffuse over at least one of the surfaces, under conditions such that the oxidizing agent brings about a polymerization of the composition when the surfaces are applied one against the other. This application may be carried out, for example, by spraying or impregnating the composition according to the invention, or alternatively a resorbable biomaterial according to the invention containing an oxidizing agent may be interposed between the two surfaces, the two surfaces having been impregnated with the composition according to the invention, or alternatively a composition in the form of a biomaterial according to the invention may be interposed between the two surfaces to be joined together.

EXAMPLE 14

150 microlitres of a solution of adhesive monomer (3), (4), (5), (6), (7), (8) or (9), (60 mg) according to one of Examples 4, 5, 8, 9 and 10, preferably 9, are deposited. A compress containing an oxidizing solution, for example iodine solution or hydrogen peroxide solution, is placed between the two tissues and the two tissues are joined together on either side of the collagen compress while maintaining a pressure, preferably for a period of a few minutes. Instead of being made of collagen, the compress may, for example, be made of alginate, of hyaluronic acid or of oxidized cellulose.

EXAMPLE 15

ADHESION OF THE SKIN IN PLASTIC AND REPARATORY SURGERY

The muscle area is brushed with the oxidizing solution and, after the surplus solution has been removed using a compress, a liquid adhesive composition according to the invention is then sprayed onto the muscle area, after which the two tissues are joined together.

This example may be applied to any surgery for maintaining two tissues in a cohesive manner, it being possible for one or both of the surfaces to be brushed, either with oxidizing solution or with the composition according to the invention, after which a spraying is carried out, either with the composition or with the oxidizing solution, before joining the tissues together.

EXAMPLE 16 PROTECTION OF ANASTOMOSES

The invention may be used for protecting anastomoses during vascular, visceral, gynaecological or urological surgery. After spraying a solution of adhesive monomer composition according to the invention on the surface of the anastomosis, an anastomosis compress or compression patch impregnated with the oxidizing solution is placed on the tissue thus covered with adhesive monomer.

As a variant, the anastomosis may be surrounded by an anastomosis patch or compress which has been preimpregnated with adhesive monomer, followed by spraying the oxidizing solution onto the material in order to obtain its adhesion to the tissue.

EXAMPLE 17

TISSUE FILLING

Following an exeresis of soft tissue or bone tissue, the cavity to be filled is covered with adhesive monomer according to Example 9 and a suspension of collagen ballotini which has been partially impregnated with the oxidizing solution is then introduced in order to fill the cavity.

As a variant, the cavity may be filled with a suspension of ballotini or a collagen solution which has been impregnated with the adhesive monomer, followed by injection of an oxidizing solution of aqueous iodine into the filled volume.

EXAMPLE 18

TISSUE RECONSTITUTION

During surgery on the dura mater, after exeresis of the pathological tissue, a patch, for example a collagen patch, is introduced in order to replace the excised tissue and to allow the formation of new tissue. Adhesive monomer composition is deposited around the edge of the patch and it is then placed in position and sprayed with the oxidizing solution in order to ensure adhesion and sealing of the gluing.

EXAMPLE 19

TISSUE PROTECTION

In order to protect an internal tissue such as a mucous membrane or an external tissue, or in order to improve a cicatrization, the tissue is impregnated with the oxidizing preparation, the surplus oxidizing solution is removed, if necessary, and an adhesive monomer composition is sprayed on. It is subsequently possible to introduce a protective compress, for example one made of collagen.

EXAMPLE 20

HAEMOSTASIS PROCESS

In case of serious bleeding in cardiovascular, abdominal or thoracic surgery, for example during hepatectomy, a solution of adhesive monomer according to the invention is sprayed onto the tissue slice and a compress which has been preimpregnated with oxidizing solution is applied, and the compression is maintained until haemostasis is obtained.

Where appropriate, in particular in the case of light bleeding, haemostasis may be achieved by the simple application of adhesive monomer and of the oxidizing solution by spraying in a successive or concomitant manner.

We claim:

1. Adhesive, biocompatible, biodegradable and non-toxic composition for surgical use, in particular for binding biological tissues together or for binding a tissue and an implanted biomaterial, said composition being polymerizable and/or cross-linkable to form multidirectional networks, wherein the adhesive composition comprises at least an organic product containing at least two thiol functions and carboxylic functions, which may be protected or unprotected, and/or carbonyl functions, of the following general formula:

$$R_3-S-(CH_2)_x-CH-NH-C-R-C-NH-CH-(CH_2)_y-S-R_4 \quad (I)$$
$$\begin{array}{cccc} | & \| & \| & | \\ C=O & O & O & C=O \\ | & & & | \\ R_1 & & & R_2 \end{array}$$

in which:

$x$ and $y=1$ or 2,

R is a hydrocarbon chain containing from 1 to 50 carbon atoms, which is optionally substituted by a hydroxy, amino, acid or ester group, with the proviso that the radical —CO—R—CO— is different from citric acid residue, $R_1$ and $R_2$ are identical or different and are chosen from the following groups:

$$-O-R_5; \; -NH-CH-(CH_2)_z-S-R_6; \; -NH-(CH_2)_y-S-R_6$$
$$\qquad\qquad\quad | $$
$$\qquad\qquad\quad COOR_7$$

wherein $z=1$ or 2, $R_3$, $R_4$, $R_5$, $R_6$ and $R_7$ independently represent hydrogen or an aliphatic and/or alicyclic and/or aromatic group, with the proviso that when said organic product comprises only two thiol functions, the composition includes also at least another organic product of the general formula (I) having at least three thiol functions.

2. Composition according to claim 1, wherein $R_1$ and $R_2$ represent —O—$R_5$.

3. Composition according to claim 1, wherein $R_1$ represents:

$$-NH-CH-(CH_2)_z-S-R_6$$
$$\quad | $$
$$\quad COOR_7$$

and $R_2$ represents —O—$R_5$ or vice versa.

4. Composition according to claim 1, wherein $R_1$ and $R_2$ consist of the radical

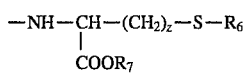

5. Composition according to claim 1, wherein R is chosen such that the radical:

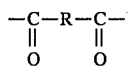

in the formula (I) is a radical belonging to the class of the polycarboxylic, acid residues.

6. Composition according to claim 1, wherein R is composed of low-molecular-weight polylactic and/or polyglycolic and/or polyamino acid chains.

7. Composition according to claim 1, wherein it is provided in bioresorbable liquid solution, spray, gel or particle form or in the form of a bulk material.

8. Adhesive material according to claim 1, which comprises a combination of at least one of the products and/or polymers and/or crosslinked materials and/or compositions according to claim 1 with biological macromolecules, or synthetic or natural biodegradable polymers selected from the group consisting of:

polysaccharides;

proteins;

polyamine acids;

polyesters, polyortho esters, polyanhydrides, polyphosphazines;

and lipids and phospholipids.

9. Adhesive composition according to claim 8, wherein the polysaccharides are selected from the group consisting of starch, cellulose, chitosan, dextran, hyaluronic acid, chondroitin sulphate, and other mucopolysaccharides.

10. Adhesive composition according to claim 8, wherein the proteins are selected from the group consisting of collagen, gelatin, albumin and globulins.

11. Adhesive composition according to claim 8, wherein the polyesters are selected from the group consisting of lactic and glycolic polyesters.

12. Composition according to claim 1 wherein R is an alkylated chain containing 1 to 50 carbon atoms.

13. Compsotion according to claim 1 wherein R is an aliphatic chain of 1 to 10 carbon atoms.

14. Composition according to claim 1 wherein $R_3$, $R_4$, $R_5$, $R_6$, and $R_7$ independently represent a lower alkyl and/or an aromatic group.

15. Composition according to claim 1 wherein $R_3$, $R_4$, $R_5$ and $R_6$ and independently represent one of the following, groups:

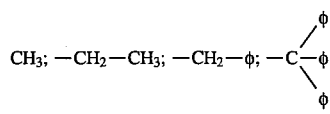

wherein 100 is an aromatic ring, at least one of $R_3$, $R_4$ and $R_6$ representing hydrogen or a $-C(\phi)_3$ group.

16. Composition according to claim 5 wherein the polycarboxylic acid residues are dicarboxylic acid residues, 17. Compositions according to claim 5 wherein R is selected from the following groups:

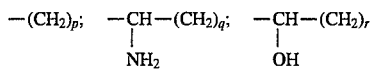

with:

$p \leq 5$, $q \geq 5$, and finallly $r \leq 5$.

* * * * *